US012742074B2

(12) United States Patent
Smith et al.

(10) Patent No.: US 12,742,074 B2
(45) Date of Patent: Sep. 22, 2026

(54) ANTIMICROBIAL PAINT COMPOSITION

(71) Applicant: Kraton Polymers LLC, Houston, TX (US)

(72) Inventors: James D Smith, Houston, TX (US); Vijay Mhetar, Houston, TX (US); Roger Tocchetto, Houston, TX (US); Bert Krutzer, Almere (NL)

(73) Assignee: Kraton Corporation, The Woodlands, TX (US)

( * ) Notice: Subject to any disclaimer, the term of this patent is extended or adjusted under 35 U.S.C. 154(b) by 498 days.

(21) Appl. No.: 17/995,854

(22) PCT Filed: Apr. 19, 2021

(86) PCT No.: PCT/US2021/070421

§ 371 (c)(1),
(2) Date: Oct. 8, 2022

(87) PCT Pub. No.: WO2021/212155

PCT Pub. Date: Oct. 21, 2021

(65) Prior Publication Data

US 2023/0151226 A1 May 18, 2023

Related U.S. Application Data

(60) Provisional application No. 63/200,304, filed on Feb. 28, 2021, provisional application No. 63/019,634, filed on May 4, 2020, provisional application No. 63/011,576, filed on Apr. 17, 2020.

(51) Int. Cl.

| | |
|---|---|
| ***C09D 5/14*** | (2006.01) |
| ***A61L 2/232*** | (2006.01) |
| ***A61L 101/48*** | (2006.01) |
| ***C08K 5/19*** | (2006.01) |
| ***C09D 7/20*** | (2018.01) |
| ***C09D 7/63*** | (2018.01) |
| ***C09D 153/00*** | (2006.01) |

(52) U.S. Cl.

CPC ................ *C09D 5/14* (2013.01); *A61L 2/232* (2013.01); *C09D 7/20* (2018.01); *C09D 7/63* (2018.01); *C09D 153/005* (2013.01); *A61L 2101/48* (2020.08); *C08K 5/19* (2013.01)

(58) Field of Classification Search

CPC ... C09D 5/14; C09D 7/20; C09D 7/63; C09D 153/005; C09D 5/1637; C09D 153/025; C09D 171/00; C09D 201/02; A61L 2/232; A61L 2101/48; C08K 5/19

See application file for complete search history.

(56) References Cited

U.S. PATENT DOCUMENTS

| | | | | |
|---|---|---|---|---|
| 3,642,953 | A * | 2/1972 | O'Neill | C08F 8/36 525/344 |
| 7,737,224 | B2 * | 6/2010 | Willis | B01D 71/401 526/287 |
| 2003/0203991 | A1 | 10/2003 | Schottman | |
| 2004/0142910 | A1 | 7/2004 | Vachon | |
| 2007/0021569 | A1 | 1/2007 | Willis | |
| 2009/0078119 | A1 | 3/2009 | Buckley | |
| 2010/0087769 | A1 | 4/2010 | Bukshpan et al. | |
| 2010/0272768 | A1 | 10/2010 | Bukshpan et al. | |
| 2011/0268901 | A1 | 11/2011 | Handlin, Jr. et al. | |
| 2013/0052153 | A1 | 2/2013 | Lin | |
| 2014/0171518 | A1 | 6/2014 | Vachon | |
| 2014/0370306 | A1 | 12/2014 | Park | |
| 2015/0024017 | A1 | 1/2015 | Bukshpan | |
| 2016/0032036 | A1 | 2/2016 | Okazaki | |
| 2017/0304815 | A1 * | 10/2017 | Vachon | C08L 57/06 |
| 2020/0016545 | A1 | 1/2020 | Seo et al. | |

FOREIGN PATENT DOCUMENTS

| | | | |
|---|---|---|---|
| CA | 2241381 | A | 12/1998 |
| CN | 104310795 | A | 1/2015 |
| CN | 108653796 | A | 10/2018 |
| EP | 1669093 | A1 | 6/2006 |
| EP | 2947483 | A1 | 11/2015 |
| JP | H11 240807 | A | 9/1999 |
| JP | 2011136977 | A * | 7/2011 |
| JP | 2013193966 | A * | 9/2013 |

(Continued)

OTHER PUBLICATIONS

English Translation of JP-2013193966-A (Year: 2013).*
English Translation of JP-2011136977-A (Year: 2011).*

*Primary Examiner* — Mark Eashoo
*Assistant Examiner* — Cullen L G Davidson

(57) ABSTRACT

An antimicrobial paint is disclosed. The antimicrobial paint comprises a carrier fluid, a binder, a sulfonated polymer and optionally at least an additive. The sulfonated polymer is selected from the group of perfluorosulfonic acid polymers, polystyrene sulfonates, sulfonated block copolymers, sulfonated polyolefins, sulfonated polyimides, sulfonated polyamides, sulfonated polyesters, sulfonated polysulfones such as polyether sulfone, sulfonated polyketones such as polyether ketone, sulfonated poly(arylene ether), and mixtures thereof. The sulfonated polymer is sufficiently or selectively sulfonated to contain from 10-100 mol % sulfonic acid or sulfonate salt functional groups based on the number of monomer units, for killing at least 99% of microbes in less than 30 minutes, or in less than 5 minutes of coming into contact with a substrate coated in the antimicrobial paint composition.

14 Claims, No Drawings

(56) References Cited

FOREIGN PATENT DOCUMENTS

| | | | |
|---|---|---|---|
| KR | 2015 0137721 | A | 12/2015 |
| WO | 99/47579 | A1 | 9/1999 |
| WO | 2006/017245 | A2 | 2/2006 |
| WO | 2007/007115 | A2 | 1/2007 |
| WO | 2009/076722 | A1 | 6/2009 |
| WO | 2009/146412 | A1 | 12/2009 |

* cited by examiner

ANTIMICROBIAL PAINT COMPOSITION

TECHNICAL FIELD

The disclosure relates to a paint composition for protecting surfaces, e.g., walls, sidings, substrates, etc., for killing microorganisms upon contact with the surfaces.

BACKGROUND

Antimicrobial biocides are substances used to destroy or suppress the growth of harmful microorganisms, such as algae, bacteria, viruses or fungi. Antimicrobial biocides have a wide array of applications in both public health-related products, for the control of organisms infectious to humans, and products other than those related to public health, such as agents in lacquers, sealants, primers, coatings, etc. for application onto construction materials, metal, masonry, wood, etc.

Consumers typically expect an aesthetic look of painted surfaces to be desirable and to have longevity; however, fungal and algal growth often stains paint, causes odor, and deteriorates the paint's properties. Accordingly, biocides can be added to paint compositions to maintain the integrity, and to provide protection in the coating against fungal and algal growth. As such, biocides for coating protection play a large role in maintaining paint's physical aesthetic and minimize microbial growth. However, most common commercial solid film biocides are based on actives that are effective against only fungi, such as molds and yeasts, and sometimes algae. Additionally, common metal-based solid film biocides may also contribute to paint discoloration when exposed to light.

There is a need for a paint composition, which can at least kill 95% microorganisms, including algae, bacteria, viruses or fungi, in a short period of time upon contact with the surface or substrate being coated or protected by the paint.

SUMMARY

The disclosure is directed to an antimicrobial paint composition. In embodiments, the paint composition comprises: a carrier fluid selected from water, solvents, liquid polymers, and combinations thereof; a sulfonated polymer; optionally a binder; optionally at least an additive. The sulfonated polymer is selected from selected from the group of perfluorosulfonic acid polymers, polystyrene sulfonates, sulfonated block copolymers, sulfonated polyolefins, sulfonated polyimides, sulfonated polyamides, sulfonated polyesters, sulfonated polysulfones, sulfonated polyketones, sulfonated poly(arylene ether), and mixtures thereof. The sulfonated polymer has a degree of sulfonation of at least 10%. The optional additives are selected from fillers, elution additives, coalescing aids, surfactants, wetting agents, thickeners, rheology modifiers, defoamers, compatibilizers, plasticizers, tackifiers, surfactants, cross-linkers, UV absorbers, highly conjugated particles, or tubes (e.g. carbon black, graphene, carbon nanotubes) and combination thereof. The sulfonated polymer is present in the paint composition in a sufficient amount for a surface coated with the antimicrobial paint composition to have a coating of sulfonated polymer of >1 μm to kill at least 90% microbes in contact with the coated surface within 120 minutes.

In another embodiment, a method of making an antimicrobial paint composition is disclosed. The method comprises the steps comprising: providing a sulfonated polymer in the form of crumbs, films, membranes, fiber, or dispersion in water or solvent; optionally removing the solvent and co-solvent; dissolving the sulfonated polymer in a solvent and optionally a co-solvent forming a sulfonated polymer solution; and mixing the sulfonated polymer solution with at least a liquid carrier or binder. The method for making the antimicrobial paint further comprises optionally mixing in at least an additive selected from pigments, fillers, elution additives, coalescing aids, surfactants, thickeners, rheology modifiers, defoamers, compatibilizers, plasticizers, tackifiers, surfactants, cross-linkers, UV absorbers, highly conjugated particles, or tubes (e.g. carbon black, graphene, carbon nanotubes) and combination thereof. The sulfonated polymer is selected from the group of perfluorosulfonic acid polymers such as sulfonated tetrafluoroethylene, polystyrene sulfonates, sulfonated block copolymers, polysulfones such as polyether sulfone, sulfonated polyether ketone sulfonated poly(arylene ether), and combination thereof. A substrate coated with the antimicrobial paint composition kills at least 95% microbes in contact with the substrate within 30 minutes.

DETAILED DESCRIPTION

The following terms used in the specification have the following meanings:

"Paint" refers to lacquers, sealants, primers, coatings, etc. which can be applied to a surface and/or substrate including but not limited to indoor and outdoor objects/structures such as walls, doors, construction material including wall board (drywall) and ceiling tiles; metals such as metal pipes and surfaces; masonry; wood, decking; marine surfaces including docks, boats, ships, etc.; sidings; porous or semi-porous materials including stone, bricks; concrete, unglazed tiles, stucco, grout, and painted surfaces. "Paint" can be applied with a brush, a roller, a spray, etc. It can also be poured out, brushed onto, or sprayed onto a surface.

"Dispersed," "dispersion," or "emulsion" refers to a two-phase system wherein one phase comprises finely divided particles distributed throughout a second phase, which is a bulk substance. The particles are the disperse or internal phase, and the bulk substance the continuous or external phase. The continuous phase can be water, an aqueous mixture, or a solvent. By "dispersion," it is also meant that not necessarily all of the polymer needs to be water-insoluble or insoluble in the organic solvent continuous phase.

"Substrate" refers to a layer under something else to provide support, having at least one surface available to deposit or coat a material of the choice.

"Effective amount" refers to an amount sufficient to alter, destroy, inactivate, neutralize and/or inhibit growth of microorganisms, e.g., an amount sufficient to sterilize and kill microorganisms in contact with the paint composition comprising the sulfonated polymer.

"Ion Exchange Capacity" or IEC refers to the total active sites or functional groups responsible for ion exchange in a polymer. Generally, a conventional acid-base titration method is used to determine the IEC, see for example International Journal of Hydrogen Energy, Volume 39, Issue 10, Mar. 26, 2014, Pages 5054-5062, "Determination of the ion exchange capacity of anion-selective membrane." IEC is the inverse of "equivalent weight" or EW, which the weight of the polymer required to provide 1 mole of exchangeable protons.

"Microorganisms" refer to organisms with microscopic size including bacteria, archaea, fungi (yeasts, molds and mildews), algae, protozoa, and viruses including coronavirus.

"Surface pH" refers to the pH on the contact surface of the bio-secure material, that results from surface bound moieties e.g., the coating layer. The surface pH can be measured with commercial surface pH measuring instruments, e.g., SenTix™ Sur-electrode from WTW Scientific-Technical Institute GmbH, Weilheim, Germany.

The disclosure relates to a paint composition comprising a sulfonated polymer for use in paint, as a coating layer of surfaces, providing antimicrobial properties. In embodiments, the paint composition comprises, consists essentially of, or consists of a sulfonated polymer, a carrier fluid, and a binder. The sulfonated polymer is employed in the paint in an amount sufficient for at least 95% microorganisms that come into contact with the surfaces protected by the paint within a pre-defined period.

Self-sterilizing Material—Sulfonated Polymer: Sulfonated polymer refers to polymers having a sulfonate group, e.g., $—SO_3$, either in the acid form (e.g., $—SO_3H$, sulfonic acid) or a salt form (e.g., $—SO_3Na$). The term "sulfonated polymer" also covers sulfonate containing polymers, e.g., polystyrene sulfonate.

The sulfonated polymer is selected from the group of perfluorosulfonic acid polymers (e.g., sulfonated tetrafluoroethylene), sulfonated polyolefins, sulfonated polyimides, sulfonated polyamides, sulfonated polyester, polystyrene sulfonates, sulfonated block copolymers, sulfonated polyolefins, sulfonated polysulfones such as polyether sulfone, sulfonated polyketones such as polyether ether ketone, sulfonated polyphenylene ethers, and mixtures thereof.

The sulfonated polymer is characterized as being sufficiently or selectively sulfonated to contain from 10-100 mol % sulfonic acid or sulfonate salt functional groups based on the number of monomer units or the block to be sulfonated ("degree of sulfonation"), to kill at least 95% of microbes within 120 minutes of coming into contact with the coating material. In embodiments, the sulfonated polymer has a degree of sulfonation of >25 mol %, or >50 mol %, or <95 mol %, or 25-70 mol %. Degree of sulfonation can be calculated by NMR or ion exchange capacity (IEC).

In embodiments, the sulfonated polymer is a sulfonated tetrafluoroethylene, having a polytetrafluoroethylene (PTFE) backbone; (2) side chains of vinyl ethers (e.g., $—O—CF_2—CF—O—CF_2—CF_2—$) which terminate in sulfonic acid groups in a cluster region.

In embodiments, the sulfonated polymer is a polystyrene sulfonate, examples include potassium polystyrene sulfonate, sodium polystyrene sulfonate, a co-polymer of sodium polystyrene sulfonate and potassium polystyrene sulfonate (e.g., a polystyrene sulfonate copolymer), having a molecular weight of 20,000 to 1,000,000 Daltons, or >25,000 Daltons, or >40,000 Dalton, or >50,000, or >75,000, or >100,000 Daltons, or >400,000 Daltons, or <200,000, or <800,000 Daltons, or up to 1,500,000 Daltons. The polystyrene sulfonate polymers can either be crosslinked or uncrosslinked. In embodiments, the polystyrene sulfonate polymers are uncrosslinked and water soluble.

In embodiments, the sulfonated polymer is a polysulfone, selected from the group of aromatic polysulfones, polyphenylenesulfones, aromatic polyether sulfones, dichlorodiphenoxy sulfones, sulfonated substituted polysulfone polymers, and mixtures thereof. In embodiments, the sulfonated polymer is a sulfonated polyethersulfone copolymer, which can be made with reactants including sulfonate salts such as hydroquinone 2-potassium sulfonate (HPS) with other monomers, e.g., bisphenol A and 4-fluorophenyl sulfone. The degree of sulfonation in the polymer can be controlled with the amount of HPS unit in the polymer backbone.

In embodiments, the sulfonated polymer is a sulfonated polyether ketone. In embodiments, the sulfonated polymer is a sulfonated polyether ketone ketone (SPEKK), obtained by sulfonating a polyether ketone ketone (PEKK). The polyether ketone ketone can be manufactured using diphenyl ether and a benzene dicarbonic acid derivative. The sulfonated PEKK can be available as an alcohol and/or water-soluble product, e.g., for subsequent use to coat the face mask or in spray applications.

In embodiments, the sulfonated polymer is a sulfonated poly(arylene ether) copolymer containing pendant sulfonic acid groups. In embodiments, the sulfonated polymer is a sulfonated poly(2,6-dimethyl-1,4-phenylene oxide), commonly referred to as sulfonated polyphenylene oxide. In embodiments, the sulfonated polymer is a sulfonated poly (4-phenoxybenzoyl-1,4-phenylene) (S-PPBP). In embodiments, the sulfonated polymer is a sulfonated polyphenylene having 2 to 6 pendant sulfonic acid groups per polymer repeat, and characterized as having 0.5 meq $(SO_3H)$/g of polymer to 5.0 meq $(SO_3H)$/g polymer, or at least 6 meq/g $(SO_3H)$/g polymer.

In embodiments, the sulfonated polymer is a sulfonated polyamide, e.g. aliphatic polyamides such nylon-6 and nylon-6,6, partially aromatic polyamides and polyarylamides such as poly(phenyldiamidoterephthalate), provided with sulfonate groups chemically bonded as amine pendant groups to nitrogen atoms in the polymer backbone. The sulfonated polyamide can have a sulfonation level of 20 to up to 100% of the amide group, with the sulfonation throughout the bulk of the polyamide. In embodiments, the sulfonation is limited to a high density of sulfonate groups at the surface, e.g., >10%, >20%, >30%, or >40%, or up to 100% of the sulfonated amide group at the surface (within 50 nm of the surface).

In embodiments, the sulfonated polymer is a sulfonated polyolefin, containing at least 0.1 meq, or >2 meq, or >3 meq, or >5 meq, or 0.1 to 6 meq of sulfonic acid per gram of polyolefin. In embodiments, the sulfonated polymer is a sulfonated polyethylene. The sulfonated polyolefin can be formed by chlorosulfonation of a solid polyolefin obtained by polymerization of an olefin or a mixture of olefins selected from a group consisting of ethylene, propylene, butene-1,4-methylpentene-1, isobutylene, and styrene. The sulfonyl chloride groups can then be hydrolyzed, for example, in an aqueous base such as potassium hydroxide or in a water dimethylsulfoxide (DMF) mixture to form sulfonic acid groups. In embodiment, the sulfonated polyolefin is formed by submerging or passing polyolefin object in any form of powder, fiber, yarn, woven fabric, a film, a preform, etc., through a liquid containing sulfur trioxide $(SO_3)$, a sulfur trioxide precursor (e.g., chlorosulfonic acid, $HSO_3Cl$), sulfur dioxide $(SO_2)$, or a mixture thereof. In other embodiments, the polyolefin object is brought into contact with a sulfonating gas, e.g., $SO_2$ or $SO_3$, or gaseous reactive precursor, or a sulfonation additive that evolves a gas $SO_x$ at elevated temperature.

The polyolefin precursor to be sulfonated can be, for example, a poly-α-olefin, such as polyethylene, polypropylene, polybutylene, polyisobutylene, ethylene propylene rubber, or a chlorinated polyolefin (e.g., polyvinylchloride, or PVC), or a polydiene, such as polybutadiene (e.g., poly-1,3-butadiene or poly-1,2-butadiene), polyisoprene, dicyclopentadiene, ethylidene norbornene, or vinyl norbornene, or a homogeneous or heterogeneous composite thereof, or a copolymer thereof (e.g., EPDM rubber, i.e., ethylene propylene diene monomer). In embodiments, the polyolefin is selected from low density polyethylene (LDPE), linear low density polyethylene (LLDPE), very low density polyethylene (VLDPE), high density polyethylene (HDPE), medium density polyethylene (MDPE), high molecular weight polyethylene (HMWPE), and ultra-high molecular weight polyethylene (UHMWPE).

In embodiments, the sulfonated polymer is a sulfonated polyimide, e.g., aromatic polyimides in both thermoplastic and thermosetting forms, having excellent chemical stability and high modulus properties. Sulfonated polyimide can be prepared by condensation polymerization of dianhydrides with diamines, wherein one of the monomeric units contains sulfonic acid, sulfonic acid salt, or sulfonic ester group. The polymer can also be prepared by direct sulfonation of aromatic polyimide precursors, using sulfonation agents such as chlorosulfonic acid, sulfur trioxide and sulfur trioxide complexes. In embodiments, the concentration of sulfonic acid groups in the sulfonated polyimide as measured by ion exchange capacity, IEC, varying from 0.1 meq/g to above 3 meq/g, or at least 6 meq/g.

In embodiments, the sulfonated polymer is a sulfonated polyester, formed by directly sulfonating a polyester resin in any form, e.g., fiber, yarn, woven fabric, film, sheet, and the like, with a sulfuric anhydride-containing gas containing sulfuric anhydride, for a concentration of the sulfone group on the surface of the polyester ranging from 0.1 meq/g to above 3 meq/g, e.g., up to 5 meq/g, or at least 6 meq/g.

In embodiments, the sulfonated polymer is a selectively sulfonated negative-charged anionic block copolymer. The term "selectively sulfonated" definition to include sulfonic acid as well as neutralized sulfonate derivatives. The sulfonate group can be in the form of metal salt, ammonium salt or amine salt.

Depending on the applications and the desired properties, the sulfonated polymer can be modified (or funcationalized). In embodiments, the sulfonated polymer is neutralized with any of various metal counterions, including alkali, alkaline earth, and transition metals, with at least 10% of the sulfonic acid groups being neutralized. In embodiments, the sulfonated polymer is neutralized with inorganic or organic cationic salts, e.g, those based on ammonium, phosphonium, pyridinium, sulfonium and the like. Salts can be monomeric, oligomeric, or polymeric. In embodiments, the sulfonated polymer is neutralized with various primary, secondary, or tertiary amine-containing molecules, with >10% of the sulfonic acid or sulfonate functional groups being neutralized.

In embodiments, the sulfonic acid or sulfonate functional group is modified by reaction with an effective amount of polyoxyalkyleneamine having molecular weights from 140 to 10,000. Amine-containing neutralizing agents can be mono-functional or multi-functional; monomeric, oligomeric, or polymeric. In alternative embodiments, the sulfonated polymer is modified with alternative anionic functionalities, such as phosphonic acid or acrylic and alkyl acrylic acids.

In embodiments, amine containing polymers are used for the modification of the sulfonated polymers, forming members of a class of materials termed coaservates. In examples, the neutralizing agent is a polymeric amine, e.g., polymers containing benzylamine functionality. Examples include homopolymers and copolymers of 4-dimethylaminostyrene which has been described in U.S. Pat. No. 9,849,450, incorporated herein by reference. In embodiments, the neutralizing agents are selected from polymers containing vinylbenzylamine functionality, e.g., polymers synthesized from poly-p-methylstyrene containing block copolymers via a bromination-amination strategy, or by direct anionic polymerization of amine containing styrenic monomers. Examples of amine functionalities for functionalization include but are not limited to p-vinylbenzyldimethylamine (BDMA), p-vinylbenzylpyrrolidine (VBPyr), p-vinylbenzyl-bis(2-methoxyethyl)amine (VBDEM), p-vinylbenzylpiperazine (VBMPip), and p-vinylbenzyldiphenylamine (VBDPA). In embodiments, corresponding phosphorus containing polymers can also be used for the functionalization of the sulfonated polymers.

In embodiments, the monomer or the block containing amine functionality or phosphine functionality can be neutralized with acids or proton donors, creating quaternary ammonium or phosphonium salts. In other embodiments, the sulfonated polymer containing tertiary amine is reacted with alkylhalides to form functional groups, e.g., quaternized salts. In some embodiments, the sulfonated polymer can contain both cationic and anionic functionality to form so-called zwitterionic polymers.

In some embodiments, the sulfonated polymer is a selectively sulfonated negative-charged anionic block copolymer, which "selectively sulfonated" definition to include sulfonic acid as well as neutralized sulfonate derivatives. The sulfonate group can be in the form of metal salt, ammonium salt or amine salt. In embodiments, the sulfonated block polymer has a general configuration A-B-A, $(A-B)_n(A)$, $(A-B-A)_nX$, $(A-B)_nX$, A-D-B, A-B-D, A-D-B-D-A, A-B-D-B-A, $(A-D-B)_nA$, $(A-B-D)_nA$ $(A-D-B)_nX$, $(A-B-D)_nX$ or mixtures thereof; where n is an integer from 0 to 30, or 2 to 20 in embodiments; and X is a coupling agent residue. Each A and D block is a polymer block resistant to sulfonation. Each B block is susceptible to sulfonation. For configurations with multiple A, B or D blocks, the plurality of A blocks, B blocks, or D blocks can be the same or different.

In embodiments, the A blocks are one or more segments selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof. If the A segments are polymers of 1,3-cyclodiene or conjugated dienes, the segments will be hydrogenated subsequent to polymerization of the block copolymer and before sulfonation of the block copolymer. The A blocks may also contain up to 15 mol % of the vinyl aromatic monomers such as those present in the B blocks.

In embodiments, the A block is selected from para-substituted styrene monomers selected from para-methylstyrene, para-ethylstyrene, para-n-propylstyrene, para-isopropyl styrene, para-n-butylstyrene, para-sec-butylstyrene, para-iso-butylstyrene, para-t-butylstyrene, isomers of para-decylstyrene, isomers of para-dodecylstyrene and mixtures of the above monomers. Examples of para-substituted styrene monomers include para-t-butylstyrene and para-methylstyrene, with para-t-butylstyrene being most preferred. Monomers may be mixtures of monomers, depending on the particular source. In embodiments, the overall purity of the para-substituted styrene monomers be at least 90%-wt., or >95%-wt., or >98%-wt. of the para-substituted styrene monomer.

In embodiments, the block B comprises segments of one or more polymerized vinyl aromatic monomers selected from unsubstituted styrene monomer, ortho-substituted styrene monomers, meta-substituted styrene monomers, alpha-methylstyrene monomer, 1,1-diphenylethylene monomer, 1,2-diphenylethylene monomer, and mixtures thereof. In addition to the monomers and polymers noted, in embodiments the B blocks also comprises a hydrogenated copolymer of such monomer (s) with a conjugated diene selected from 1,3-butadiene, isoprene and mixtures thereof, having a vinyl content of between 20 and 80 mol percent. These copolymers with hydrogenated dienes can be any of random copolymers, tapered copolymers, block copolymers or controlled distribution copolymers. The block B is selectively sulfonated, containing from about 10 to about 100 mol % sulfonic acid or sulfonate salt functional groups based on the number of monomer units. In embodiments, the degree of sulfonation in the B block ranges from 10 to 95 mol %, or 15-80 mol %, or 20-70 mol %, or 25-60 mol %, or >20 mol %, or >50 mol %.

The D block comprises a hydrogenated polymer or copolymer of a conjugated diene selected from isoprene, 1,3-butadiene and mixtures thereof. In other examples, the D block is any of an acrylate, a silicone polymer, or a polymer of isobutylene with a number average molecular weight of >1000, or >2000, or >4000, or >6000.

The coupling agent X is selected from coupling agents known in the art, including polyalkenyl coupling agents, dihaloalkanes, silicon halides, siloxanes, multifunctional epoxides, silica compounds, esters of monohydric alcohols with carboxylic acids, (e.g. methylbenzoate and dimethyl adipate) and epoxidized oils.

The antimicrobial and mechanical properties of the sulfonated block copolymer can be varied and controlled by varying the amount of sulfonation, the degree of neutralization of the sulfonic acid groups to the sulfonated salts, as well as controlling the location of the sulfonated group(s) in the polymer. In embodiments and depending on the applications, e.g., one with the need for water dispersity/solubility, or at the other spectrum, one with the need for sufficient durability with constant wiping with water based cleaners, the sulfonated block copolymer can be selectively sulfonated for desired water dispersity properties or mechanical properties, e.g., having the sulfonic acid functional groups attached to the inner blocks or middle blocks, or in the outer blocks of a sulfonated block copolymer, as in U.S. Pat. No. 8,084,546, incorporated by reference. If the outer (hard) blocks are sulfonated, upon exposure to water, hydration of the hard domains may result in plasticization of those domains and softening, allowing dispersion or solubility.

The sulfonated copolymer in embodiments is as disclosed in U.S. Pat. Nos. 9,861,941, 8,263,713, 8,445,631, 8,012,539, 8,377,514, 8,377,515, 7,737,224, 8,383,735, 7,919,565, 8,003,733, 8,058,353, 7,981,970, 8,329,827, 8,084,546, 8,383,735, 10,202,494, and 10,228,168, the relevant portions are incorporated herein by reference.

In embodiments, the sulfonated block copolymer has a general configuration A-B-$(B\text{-}A)_{1\text{-}5}$, wherein each A is a non-elastomeric sulfonated monovinyl arene polymer block and each B is a substantially saturated elastomeric alpha-olefin polymer block, said block copolymer being sulfonated to an extent sufficient to provide at least 1% by weight of sulfur in the total polymer and up to one sulfonated constituent for each monovinyl arene unit. The sulfonated polymer can be used in the form of their acid, alkali metal salt, ammonium salt or amine salt.

In embodiments, the sulfonated block copolymer is a sulfonated polystyrene-polyisoprene-polystyrene, sulfonated in the center segment. In embodiments, the sulfonated block copolymer is a sulfonated t-butylstyrene/isoprene random copolymer with C═C sites in their backbone. In embodiments, the sulfonated polymer is a sulfonated SBR (styrene butadiene rubber) as disclosed in U.S. Pat. No. 6,110,616 incorporated by reference. In embodiments, the sulfonated polymer is a water dispersible BAB triblock, with B being a hydrophobic block such as alkyl or (if it is sulfonated, it becomes hydrophilic) poly(t-butylstyrene) and A being a hydrophilic block such as sulfonated poly(vinyl toluene) as disclosed in U.S. Pat. No. 4,505,827 incorporated by reference. In embodiments, the sulfonated block copolymer is a functionalized, selectively hydrogenated block copolymer having at least one alkenyl arene polymer block A and at least one substantially completely, hydrogenated conjugated diene polymer block B, with substantially all of the sulfonic functional groups grafted to alkenyl arene polymer block A (as disclosed in U.S. Pat. No. 5,516,831, incorporated by reference). In embodiments, the sulfonated polymer is a water-soluble polymer, a sulfonated diblock polymer of t-butylstyrene/styrene, or a sulfonated triblock polymer of t-butylstyrene-styrene-t-butylstyrene as disclosed in U.S. Pat. No. 4,492,785 incorporated by reference. In embodiments, the sulfonated block copolymer is a partially hydrogenated block copolymer.

In embodiments, the sulfonated polymer is a midblock-sulfonated triblock copolymer, or a midblock-sulfonated pentablock copolymer or, e.g., a poly(p-tert-butylstyrene-b-styrenesulfonate-b-p-tert-butylstyrene), or a poly[tert-butylstyrene-b-(ethylene-alt-propylene)-b-(styrenesulfonate)-b-(ethylene-alt-propylene)-b-tert-butylstyrene.

In embodiments, the sulfonated polymer contains >15 mol %, or >25 mol %, or >30 mol %, or >40 mol %, or >60 mol % sulfonic acid or sulfonate salt functional groups based on the number of monomer units in the polymer that are available or susceptible for sulfonation, e.g., the styrene monomers.

In embodiments, the sulfonated polymer has an ion exchange capacity of >0.5 meq/g, or >0.75 meq/g, or >1.0 meq/g, or >1.5 meq/g, or >2.0 meq/g, or >2.5 meq/g, or <5.0 meq/g.

The sulfonated polymer is incorporated into the paint composition in a sufficient amount such that when the paint composition is applied onto surfaces for protection, a layer of sulfonated polymer layer provided at a surface, forming a thin protective layer comprising, consisting essentially of, or consisting of sulfonated polymer, e.g., <1000 μm, or <100 μm, or >10 μm; or in embodiments, in amount of 0.1 to 10 wt. %, or 0.5 to 5 wt. %, or <7 wt. %, or >0.5 wt %, based on total weight of the spray composition. This top surface layer in embodiments, comprises at least 50 wt. % sulfonated polymer, preferably >60 wt. %, more preferably >75 wt. %, even more preferably >85 wt. %, most preferably >95 wt. %, and most preferably >99 wt. %.

Properties of Sulfonated Polymer: In embodiments, the sulfonated polymer is characterized as being sufficiently sulfonated to have an IEC of >0.5 meq/g, or 1.5-3.5 meq/g, or >1.25 meq/g, or >2.2 meq/g, or >2.5 meq/g, or >4.0 meq/g, or <4.0 meq/g.

In embodiments, the sulfonated polymer is characterized as having a surface pH of <3.0, or <2.5, or <2.25, or <2.0, or <1.80. It is believed that a sufficiently low surface pH level, as a result of the presence of sulfonic acid functional groups in the paint composition, kills microorganisms that come in contact with the paint surface, including bacteria, viruses, algae, mold, mildew, and fungi in the environment (e.g., air or water).

In embodiments, the sulfonated polymer works effectively in destroying/inactivating >90%, or >95, or >99%, or >99.5%, or >99.9% of microorganisms within <120 minutes of exposure, <60 minutes exposure, <30 minutes of exposure, or <5 minutes of exposure or contact with microorganisms, including but not limited to MRSA, vancomycin-resistant *Enterococcus faecium*, X-MulV, PI-3, SARS-CoV-2, carbapenem-resistant *Acinetobacter baumannii*, and influenza A virus. In embodiments with polymer containing quaternary ammonium group, the material is effective in killing target microorganisms including *Staphylococcus aureus, Escherichia coli, Staphylococcus albus, Escherichia coli, Rhizoctonia solani*, and *Fusarium oxysporum*. The sulfonated polymer remains effective in killing microbes even after 4 hours, or after 12 hours, or at least 24 hours, or for at least 48 hours. In embodiments, the sulfonated polymer remains effective in killing microbes for at least 3 months, or for at least 6 months.

The sulfonated polymer contains from 10-100 mol % sulfonic acid or sulfonate salt functional groups based on the number of monomer units or blocks in the sulfonated polymer susceptible to sulfonation (i.e., can be sulfonated), for the coating material to kill at least 95% of microbes within 120 minutes of contact. In tests simulating cleaning of the surface of a sulfonated polymeric film, after 2400 cleaning or abrasion cycle, representing 200 days (at least 6 months) in use with 6 cleaning sessions per day (with 4 rubbing motions per session with alcohol and/or quaternary ammonium compounds cleaners).

Liquid Carrier: The paint compositions comprise a liquid carrier. Any suitable liquid carrier can be used, such as a solvent, a liquid polymer, or combinations thereof. The liquid carrier may be aqueous, organic, or combinations thereof. The liquid carrier disperses and may solubilize, partially solubilize, or dissolve the other components of the paint composition.

In embodiments, the carrier is aqueous, e.g., water, although solvents that are miscible with water can be used as co-solvents. Examples of suitable co-solvents include ethers, esters, alcohols, glycols, aromatics, and the like. Specific examples include ethylene glycol or a derivative thereof, such as ethylene glycol monoethyl ether, ethylene glycol monobutyl ether, diethylene glycol monobutyl ether, or ethylene glycol monohexyl ether; propylene glycol or a derivative thereof, such as propylene glycol monomethyl ether, propylene glycol monoethyl ether, or propylene glycol monobutyl ether; or combinations thereof.

In embodiments, the aqueous liquid carrier consists of, or consists essentially of water. In embodiments, co-solvents are used along with water.

In embodiments, the carrier is non-aqueous, e.g., an organic carrier. Examples include but not limited to aromatic materials such as benzene, xylene, toluene, low-boiling ethers, esters, alcohols, ketones such as butyl acetate, methyl isobutyl ketone, methyl amyl ketone, and mixtures thereof. In embodiments, the carrier is selected from paint thinner, denatured alcohol, and lacquer thinner.

The liquid carrier, water or an organic carrier, is present in an effective amount, e.g. for creating a solution or emulsion when mixed with the other components of the paint composition, such as 20-80 wt. %, 30-75 wt. %, or >10 wt. %, or <90 wt. %, based on the total weight of the paint composition.

In embodiments, it may be desirable to adjust the pH of the liquid carrier, depending, for example, on whether one or more components in the paint composition may perform better for certain end uses based on the pH of the liquid carrier, e.g., effectiveness of the sulfonated polymer in killing microbes.

Binder: In embodiments, the paint composition also comprises a binder. The binder is typically a resin, a tackifier, waxes, such as a thermoset, a thermoplastic, or combinations thereof. The binders may be natural or synthetic; reactive or nonreactive; crosslinked or uncrosslinked; organic or inorganic; linear, branched, resinous, polymeric, oligomeric, or a combination thereof; hydrophilic or hydrophobic; lipophilic or lipophobic; charged or uncharged; polar or nonpolar; and combinations thereof. In embodiments, binders are dispersible in the liquid carrier.

Depending on the sulfonated polymers employed in the paint composition, in embodiments, the selected binder has a molecular weight that is more than 10%, or more than 20%, or more than 40% than the molecular weight of the sulfonated polymer, allowing the sulfonated polymer to be formed as the top surface layer of the paint coating. In embodiments, the selection is based on the surface energy, with the sulfonated polymer having a surface energy that is less than that of the binder, e.g., at least 10% less than, or at least 20% less than, or at least 30% less than the surface energy of the selected binder, allowing the sulfonated polymer to be the top surface layer of the paint coating.

In embodiments, the binder is selected from modified rosins, phenolic resins, rosin esters, acrylics, polyurethanes, silicones, acrylates, solution polymers, polyvinyl acetate, polyvinyl chloride, styrene-butadiene rubber, other styrene polymers, acrylonitrile-butadiene rubber, epoxy resins, polyacrylics, and combinations thereof. In embodiments, the binder is selected such that the paint composition is a polyurethane dispersion, a silicone emulsion, a styrene acrylate dispersion, a urethane-acrylic hybrid dispersion, an aliphatic polyurethane dispersion, an acrylic dispersion, tackifier resins, or combinations thereof. In embodiments, the binder is a fluorochemical urethane. In embodiments, the binder is polytetrafluoroethylene (PTFE), e.g., as dry powder form or a fine dispersion liquid stabilized in non-ionic surfactant with a condensed PTFE solid of up to 60%. In embodiments, the binder is a tackifier resin, selected from hydrogenated petroleum resin, petroleum aliphatic resins, alicyclic resins, rosin resins, terpene resins and hydrogenated resins thereof.

In embodiments, the binder is selected from an alkyd, alkyd oils, or oil derivative such as linseed oil, sunflower oil, tung oil, poppy seed oil, soybean oil, olive oil, or a combination thereof.

Any suitable amount of the binder can be used in the paint composition. The amount can vary depending on a variety of factors, including, but not limited to, the desired rheology of the paint composition, the desired end use of the paint composition, the properties of the binder, the identity of other components (e.g. the liquid carrier) in the paint composition, and end uses. In embodiments, the amount of binder is >2 wt. %, or >2 wt. %. or <60 wt. %, or 20-60 wt. %, or 2-55 wt. %, or 5-30 wt. %, or 30-45 wt. %, based on total weight of the paint composition.

Optional Colorant: In embodiments, the paint composition further comprises one or more colorants, such as pigments, dyes, and the like. The colorants can be organic or inorganic, synthetic or natural, alone or in combination, to produce a wide range of colored paint.

In embodiments, the antimicrobial paint composition includes a colorant comprising titanium dioxide ($TiO_2$).

The amount of colorant, if employed, is <20 wt. %, or 0.1-15 wt. %, or >2 wt. %, depending on the application and the amount of other components.

Optional Additives—Color Change Indicator: In embodiments, the paint composition further comprises additives that would help signal or give an indicator of the antimicrobial effects of the sulfonated polymer with a color change pH indicator. Examples include Thymol Blue, Methyl Orange, Bromocresol Green, Methyl Red, Bromothymol Blue, Phenol Red, and Phenol-phthalein. A color change means a change in hue, from a light to a darker color or vice versa. A color indicator may indicate if another coating, or recharge, regeneration, or reactivation of the antimicrobial activity of the paint is needed. The color indicator is incorporated in a sufficient amount so that a noticeable change in color hue is observed immediately when there is a change in the surface pH of the paint is raised above 2.0 (different pathogens have different pH responses), the change is known right away. In embodiments, the amount of color indicator ranges from 0.1 to 20 wt. % of the amount of sulfonated polymer in the paint composition.

Optional Additives—Others: In embodiments, the paint composition comprises additional components including but not limited to, fillers, elution additives, coalescing aids, surfactants, thickeners, rheology modifiers, defoamers, compatibilizers, plasticizers, tackifiers, surfactants, cross-linkers, UV absorbers, highly conjugated particles, or tubes (e.g. carbon black, graphene, carbon nanotubes) and the like. It should be noted that some of the optional additives such as oil derivatives, etc., may have functions that of binders, fragrance, etc., and the like.

In embodiments, the paint composition comprises functional fillers which are non-water soluble solids. The functional fillers may be, for example, reinforcing fillers and/or extending fillers, e.g., calcium carbonate, talc, clay, silicates, aluminum silicates, calcium metasilicates, aluminum potassium silicates, magnesium silicates, barium sulfates, nepheline syenite, feldspar, zinc oxides or sulfides, and combinations thereof.

In embodiments, the paint composition further comprises a coalescing aid. Suitable coalescing aids include any compound that decreases the minimum film-formation temperature of the binder, and/or increases the rate of solid film formation from the binder when the liquid carrier is removed.

In embodiments, the paint composition comprises a surfactant. The surfactant may be non-ionic or ionic, such as cationic, anionic, zwitterionic, and mixtures thereof. Examples include but are not limited to alkoxylate, alcohol ethyoxylate, sulfosuccinate, sulfate, sulfonate, disulfonate, phosphate ester, phenolic, or ethylene oxide/propylene oxide surfactants, or combinations thereof.

In embodiments, thickeners and/or rheology modifiers may also be added to provide desired viscosity and/flow properties, e.g., hydroxyethyl cellulose, methyl cellulose and carboxymethyl cellulose, hydropbobically modified urethane ethoxylate (HEUR) thickener, and mixtures thereof.

In embodiments, in addition to the sulfonated polymer(s), the paint composition further contains additional antimicrobials such as butylparaben and triclosan, e.g., antimicrobial surfactants, quaternary ammonium and phosphonium containing polymers, metallic-based micro and nano-structured materials such as silver, copper, zinc, titanium and their oxides, for enhanced antimicrobial effectiveness. In embodiments, the paint composition further comprises algaecide including but not limited to 3-(3,4-dichlorophenyl)-1,1-dimethylurea (diuron), 2-(tert-butylamino)-4-(cyclopropylamino)-6-(methylthio)-1,3,5-triazine (Irgarol™), and 2-(tert-butylamino)-4-(ethylamino)-6-(methylthio)-s-triazine (terbutryn). In embodiments, the paint composition further contains a mold/mildew inhibitor, e.g., zinc pyrithione, carbendazim (BCM), chlorothalonil (CTL), iodopropynylbutylcarbamate (IPBC), octylisothiazolinone (OIT), dichlorooctylisothiazolinone (DCOIT), n-butyl-benzisothiazolinone (BBIT), and zinc pyrithione (ZnPT).

Depending on the additives, optional additives may be included in amounts of >2 wt. %, <35 wt. %, or 0.1-30 wt. %, or 0.5-10 wt. %, or <5 wt. %, based on the total weight of the paint composition.

Applications: The paint composition is suited for painting surfaces in medical facilities such as hospitals and clinics, care facilities such as nurseries and assisted living homes, public buildings, and laboratories. As used herein, surfaces refer to ceilings, walls, doors, counters, fixtures, basins, pieces of furniture or machinery, etc.

The paint composition can be used for painting surfaces in other public places such as schools, offices, residential buildings, gyms, saunas, swimming pool areas, hotels, restaurants, factories, food manufacturing facilities, transportation facilities and vehicles such as cars, ambulances, buses, trains, airplanes, boats and ships, and the like.

Due to the anti-mold/anti-mildew/anti-fungal properties of sulfonated polymer, the paint composition can be applied to surfaces prone to mold, mildew, and algae, e.g., inside and outside of pipes, drains, storage tanks, boat surfaces, docks, etc., and the like.

The paint composition can also be applied to substrates such as indoor and outdoor objects/structures, construction material, metal, metal pipe, masonry, wood, decking, docks, boat, roads, siding, porous or semi-porous materials including stone, brick, wall board (drywall) and ceiling tiles, concrete, unglazed tile, stucco, grout, painted surfaces, roofing tiles, shingles, and painted or treated wood.

Methods for Incorporating Sulfonated Polymers onto/into Paint Composition:

The sulfonated polymer is added to the paint composition in a sufficient amount necessary to at least kill 95% microorganisms after application. Depending on the application (e.g., a transparent coating or a thick/decorative coating), the thickness of the paint coating (e.g., a very thin transparent/clear top coat), in embodiments, the amount of sulfonated polymer after drying ranges from 2 to 90 wt. % of the dry paint layer, or >5 wt. %, or <80 wt. %, or 10-30 wt. %. The thickness of the sulfonated polymer (antimicrobial/protective layer) on the substrate (after the paint composition has dried) ranges from 1 to 250 μm, or >1 μm, or <5 μm, or 3-100 μm, or 10-100 μm.

The sulfonated polymer is provided in the form of crumbs, films, membranes, fiber, powder, pellets, or dispersion in a solvent which can be an organic solvent or water.

In embodiments, the paint composition is prepared by combining the liquid carrier, optional binder, the sulfonated polymer, and optional components individually or in combinations, sequentially or simultaneously, or combinations thereof. The step of combining may be performed by manual or automated processes, or combinations thereof, by suitable means such as mixing, blending, stirring, and the like, and combinations thereof.

In embodiments, the sulfonated polymer for incorporation into the paint can be first prepared by dissolving into an organic solvent, water, or a non-aqueous dispersion prior to mixing with other paint components, e.g., liquid carried and the binder. If the sulfonated polymer is water dispersible and if liquid carrier is water, the sulfonated polymer can be mixed directly into the liquid carrier (e.g., water).

The solvents can include one or more aprotic polar solvents including ethers, amides, esters, ketones, nitriles, tertiary amines, sulfates and sulfoxide. In embodiments, the sulfonated polymer is applied as a solution containing aliphatic hydrocarbons like cyclohexane, in aromatic hydrocarbons like toluene, in alcohols like methanol, ethanol, propanol, benzyl alcohol and the like, in various carbonyl solvents like methylethylketone, acetone, etc., or in a nitrogen containing solvents like N-methyl pyrolidone, N,N-dimethyl acetamide, pyridine, etc.

In embodiments, the sulfonated polymer is prepared as disclosed in U.S. Pat. No. 9,988,500 incorporated by reference, by first dissolving the polymer in an apolar solvent, then mixed with a co-solvent (e.g., MEK, 1-propanol, or THF). The mixture is emulsified in water to produce an emulsion, which can be subsequently mixed with other components of the paint composition.

Methods for Application: The paint composition can be applied on substrate by any suitable technique, e.g., spraying, air spraying, airless spraying, electrostatic spraying, air-assisted airless spraying, hot spraying, rotation bell painting, rotary atomizing, coating, brush coating, powder coating, roll coating, dip coating, flow coating, curtain coating, barrel coating, electrocoating, dispersion coating, high-volume, low-pressure spray, paintbrush and the like, forming a coating/a protective layer.

In embodiments, the paint composition comprising the sulfonated polymer can be applied directly to the substrate. In embodiments, the paint composition comprising the sulfonated polymer is applied as an antimicrobial top-coat, on top of a paint layer of a different composition. In embodiments, the thickness of the layer comprising, consisting essentially of, or consisting the sulfonated polymer as the protective layer ranges between 25-200 μm, or <100 μm, or 30-75 μm, or <150 μm after drying, with the sulfonated polymer being the top surface layer, with a thickness of >1 μm, or >5 μm, or >20 μm.

The paint composition can be used in conjunction with primers, undercoats, and the like. The efficacy of the paint composition and coating formed therefrom can be defined in terms of a reduction in the total number of microorganisms in contact with the surface coated or protected with the paint containing the sulfonated polymer.

Examples: The following examples are intended to be non-limiting.

Example 1: Tests were conducted to evaluate antimicrobial efficacy & the long-lasting antiviral properties of sulfonated polymers, film samples of sulfonated penta block copolymer (SPBC) of the structure poly[tert-butylstyrene-b-(ethylene-alt-propylene)-b-(styrene-co-styrene-sulfonate)-b-(ethylene-alt-propylene)-tert-butylstyrene] with 52% sulfonation were cast out of 1:1 mixture of toluene and 1-propanol. The sulfonated polymer film samples were subjected to abrasion testing of 2200 cycles in the presence of 3 common disinfectants: 1) 70% ethanol, benzalkonium chloride, and quaternary ammonia], and exposure to SARS-CoV-2 virus suspension of concentration $10^7$ pfu/ml.

After 2 hours of contact, viable virus was recovered from each sample by washing twice with 500 μl of DMEM tissue culture media containing 10% serum, and measured by serial dilution plaque assay. Gibco Dulbecco's Modified Eagle Medium (DMEM) is a basal medium for supporting the growth of many different mammalian cells. The results demonstrate that, after abrasion testing representing approximately one year of cleaning (6 disinfectant wipes/day), surface pro Gibco Dulbecco's Modified Eagle Medium (DMEM) is a widely used basal medium for supporting the growth of many different mammalian cells.

Example 2: The example was conducted to evaluate the effectiveness in inhibiting *Aspergillus niger* black mold according to the AATCC Test Method 30-2004 Test III. Six different sulfonated block copolymer membrane samples comprising a poly[tert-butylstyrene-b-(ethylene-alt-propylene)-b-(styrenesulfonate)-b-(ethylene-alt-propylene)-b-tert-butylstyrene], at different levels of sulfonation from 26 to 52% were used for the tests. *Aspergillus niger*, ATCC#6275, was harvested into sterile distilled water containing glass beads. The flask was shaken to bring the spores into suspension. The suspension was used as the test inoculum. One (1.0) mL of the inoculum was even distributed over the surface of Mineral Salts Agar plates.

The membrane samples were placed onto the inoculated agar surface. After placement, 0.2 mL of the inoculum was distributed over the surface of each disc. A viability plate of the spore suspension was prepared on Mineral Salts Agar with 3% glucose. A positive growth control was prepared using an untreated cotton duck fabric on Mineral Salts Agar and set up in the same manner as the test items. All samples were incubated at 28° C.±1° C. for 14 days.

The viability plate had acceptable fungal growth as expected confirming the viability of the inoculum. The sample with 26% sulfonation showed microscopic growth on 10% of the sample surface. The other 5 test samples showed no growth, or microscopic growth on 1% of the surface. The control sample showed macroscopic growth on 100% of the surface.

Example 3: Various solutions of sulfonated block polymer were prepared by dissolving dried sheets of sulfonated block copolymers from Kraton Corp. in solvent systems of cyclohexane, toluene, or a blend of 1:1 toluene and 1-propanol. Solutions prepared ranged from 1%-20% solids, preferably 5%-8% solids for spraying.

Dilute solutions are poured into the spray cup reservoir of HVLP spray gun, and applied by powering the sprayer with approximately 26 psi of house air and squeezing the sprayer trigger. Coatings are applied onto different substrates, including Plexiglas, Tyvek, non-woven fabrics, surgical masks, N95 masks, medical specimen bags, mylar, stainless steel and other metals, exam gloves, solid surface countertop, decorative graphic laminate film, leather, carpet, HVAC filter media, plastic, cardboard, and glass.

Example 4: Polyether-ether-ketone is sulfonated by sulfuric acid and then purified to obtain sulfonated polyether-ether-ketone A paint composition is prepared with the following components in parts by mass, 100 parts of sulfonated polyether ether ketone, 6 parts of polytetrafluoroethylene, and 200 parts of water. The composition can be sprayed onto surfaces forming a coating layer.

As used herein, the term "comprising" means including elements or steps that are identified following that term, but any such elements or steps are not exhaustive, and an embodiment can include other elements or steps. Although the terms "comprising" and "including" have been used herein to describe various aspects, the terms "consisting essentially of" and "consisting of" can be used in place of "comprising" and "including" to provide for more specific aspects of the disclosure and are also disclosed.

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained. It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

Unless otherwise specified, all technical and scientific terms used herein have the same meanings as commonly understood by one of skill in the art to which the disclosed disclosure belongs. the recitation of a genus of elements, materials or other components, from which an individual component or mixture of components can be selected, is intended to include all possible sub-generic combinations of the listed components and mixtures thereof.

The patentable scope is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims. To an extent not inconsistent herewith, all citations referred to herein are hereby incorporated by reference.

The invention claimed is:

1. An antimicrobial paint composition comprising:

a carrier fluid selected from water, solvents, liquid polymers or waxes, and combinations thereof;

a selectively sulfonated negatively-charged block copolymer having a general configuration of: A-B-A, (A-B)n(A), (A-B-A)n, (A-B-A)$_n$X, (A-B)nX, A-D-B, A-B-D, A-D-B-D-A, A-B-D-B-A, (A-D-B)$_n$A, (A-B-D)$_n$A (A-D-B)$_n$X, (B-D-B)$_n$X, (A-B-D)$_n$X or mixtures thereof, wherein n is an integer from 0 to 30, X is a coupling agent residue, each A and D block is a polymer block resistant to sulfonation, each B block is susceptible to sulfonation, the A block is selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof;

the B block is a vinyl aromatic monomer, the D block is a hydrogenated polymer or copolymer of a conjugated diene selected from isoprene, 1,3-butadiene and mixtures thereof;

wherein the block B is selectively sulfonated such that from 10 to 100 mol % of the monomer units in block B bear sulfonic acid (—$SO_3H$) groups in their free acid form, and are not neutralized or converted to salts, esters, or other derivatives;

optionally a binder; and optionally at least an additive selected from fillers, elution additives, coalescing aids, surfactants, wetting agents, thickeners, rheology modifiers, defoamers, compatibilizers, plasticizers, tackifiers, cross-linkers, UV absorbers, highly conjugated particles, or tubes (e.g. carbon black, graphene, carbon nanotubes) and combinations thereof;

wherein the selectively sulfonated negatively-charged block copolymer is present in an amount greater than 20 and up to 90 wt. %, based on total weight of the antimicrobial paint composition after drying; and wherein the antimicrobial paint composition, when applied to a surface and dried, forms a dried coating comprising a layer of the selectively sulfonated negatively-charged block copolymer having a thickness >1 μm, and kills at least 90% of microbes in contact with the dried coating within 120 minutes; and wherein sulfonic acid (—$SO_3H$) groups of the selectively sulfonated B block are present at a surface of the dried coating in an amount sufficient to provide the dried coating with a surface pH<3.0.

2. The antimicrobial paint composition of claim 1, wherein the selectively sulfonated negatively-charged block copolymer has an ionic exchange capacity (IEC) of >0.5 meq/g.

3. The antimicrobial paint composition of claim 1, wherein the dried coating comprising a layer of the selectively sulfonated negatively-charged block copolymer has a thickness of at least >5 μm, and kills at least 95% of microbes within 120 minutes of contact.

4. The antimicrobial paint composition of claim 1, wherein a surface coated with the antimicrobial paint composition kills at least 95% of microbes within 30 minutes of contact.

5. The antimicrobial paint composition of claim 1, wherein the selectively sulfonated negatively-charged block copolymer is water dispersible.

6. The antimicrobial paint composition of claim 1, wherein the binder is selected from acrylics, polyurethanes, silicones, acrylates, solution polymers, latexes, oils, oil derivatives, polytetrafluoroethylene, tackifier resins, alkyds, alkyd oils, and combinations thereof.

7. The antimicrobial paint composition of claim 1, further comprising at least an additive selected from elution additives, coalescing aids, surfactants, wetting agents, thickeners, rheology modifiers, defoamers, UV absorbers, fragrance, oil derivatives, and mixtures thereof.

8. The antimicrobial paint composition of claim 1, wherein the paint composition is applied onto a substrate by spraying, air spraying, airless spraying, electrostatic spraying, air-assisted airless spraying, hot spraying, rotation bell painting, rotary atomizing, coating, brush coating, powder coating, roll coating, dip coating, flow coating, curtain coating, barrel coating, electrocoating, dispersion coating, high-volume, low-pressure spray, paintbrush.

9. The antimicrobial paint composition of claim 8, wherein the substrate is at least one selected from indoor and outdoor objects/structures, construction material, metal, metal pipe, masonry, wood, decking, docks, boat, roads, siding, porous or semi-porous materials including stone, brick, wall board, ceiling tiles, concrete, unglazed tile, stucco, grout, painted surfaces, roofing tiles, shingles, fabric, tents, furniture, and painted or treated wood.

10. The method of making an antimicrobial paint composition, the steps comprising:

providing a selectively sulfonated negatively-charged block copolymer in the form of crumbs, films, membranes, fiber, powder, pellets, or liquid dispersion;

mixing the selectively sulfonated negatively-charged block copolymer with a liquid carrier fluid selected from water, solvents, liquid polymers or waxes, and combinations thereof;

optionally mixing in at least a binder; and optionally mixing in at least an additive selected from the group of fillers, elution additives, coalescing aids, surfactants, thickeners, rheology modifiers, defoamers, compatibilizers, plasticizers, tackifiers, cross-linkers, UV absorbers, carbon black, graphene, carbon nanotubes, and combinations thereof;

wherein the selectively sulfonated negatively-charged block copolymer has a general configuration of: A-B-A, $(A\text{-}B)_n(A)$, (A-B-A)n, $(A\text{-}B\text{-}A)_nX$, $(A\text{-}B)_nX$, A-D-B, A-B-D, A-D-B-D-A, A-B-D-B-A, $(A\text{-}D\text{-}B)_nA$, $(A\text{-}B\text{-}D)_nA$ $(A\text{-}D\text{-}B)_nX$, $(B\text{-}D\text{-}B)_nX$, $(A\text{-}B\text{-}D)_nX$ or mixtures thereof, wherein n is an integer from 0 to 30, X is a coupling agent residue, each A and D block is a polymer block resistant to sulfonation, each B block is susceptible to sulfonation, the A block is selected from polymerized (i) para-substituted styrene monomers, (ii) ethylene, (iii) alpha olefins of 3 to 18 carbon atoms; (iv) 1,3-cyclodiene monomers, (v) monomers of conjugated dienes having a vinyl content less than 35 mol percent prior to hydrogenation, (vi) acrylic esters, (vii) methacrylic esters, and (viii) mixtures thereof;

the B block is a vinyl aromatic monomer, the D block is a hydrogenated polymer or copolymer of a conjugated diene selected from isoprene, 1,3-butadiene and mixtures thereof;

wherein the block B is selectively sulfonated such that from 10 to 100 mol % of the monomer units in block B bear sulfonic acid ($—SO_3H$) groups in their free acid form, and are not neutralized or converted to salts, esters, or other derivatives;

wherein the selectively sulfonated negatively-charged block copolymer is present in an amount greater than 20 and up to 90 of wt. % based on total weight of the antimicrobial paint composition after drying; and wherein the antimicrobial paint composition, when applied to a surface and dried, forms a dried coating comprising a layer of the selectively sulfonated negatively-charged block copolymer having a thickness of at least >1 μm, and kills at least 95% microbes in contact with the dried coating within 30 minutes; and wherein sulfonic acid ($—SO_3H$) groups of the selectively sulfonated B block are present at a surface of the dried coating in an amount sufficient to provide the dried coating with a surface pH<3.0.

11. A method to sterilize and prevent transmission of microbes from a surface prone to exposure to microbes, the method comprises coating the surface with the paint composition of claim 1.

12. The method of claim 10, wherein the selectively sulfonated negatively-charged block copolymer has an ionic exchange capacity (IEC) of >0.5 meq/g.

13. The method of claim 10, wherein the dried coating comprising a layer of the selectively sulfonated negatively-charged block copolymer has a thickness of at least >5 μm, and kills at least 95% of microbes within 120 minutes of contact.

14. The method of claim 10, wherein the surface coated with the antimicrobial paint composition kills at least 95% of microbes within 30 minutes of contact.

* * * * *